United States Patent
Verkaart et al.

(10) Patent No.: US 6,325,422 B1
(45) Date of Patent: Dec. 4, 2001

(54) FILTER BAG AND CONNECTOR CARTRIDGE

(75) Inventors: Wesley H. Verkaart; James R. Ellsworth, both of Norwell, MA (US)

(73) Assignee: Harvest Technologies Corporation, Norwell, MA (US)

( * ) Notice: Subject to any disclaimer, the term of this patent is extended or adjusted under 35 U.S.C. 154(b) by 0 days.

(21) Appl. No.: 09/051,481

(22) PCT Filed: Oct. 18, 1996

(86) PCT No.: PCT/US96/16772

§ 371 Date: Jun. 5, 1998

§ 102(e) Date: Jun. 5, 1998

(87) PCT Pub. No.: WO97/14493

PCT Pub. Date: Apr. 24, 1997

Related U.S. Application Data

(60) Provisional application No. 60/008,127, filed on Oct. 20, 1995, provisional application No. 60/008,128, filed on Oct. 20, 1995, provisional application No. 60/005,772, filed on Oct. 20, 1995, and provisional application No. 60/020,754, filed on Jun. 28, 1996.

(51) Int. Cl.[7] ..................................................... F16L 35/00
(52) U.S. Cl. ............................... 285/93; 210/85; 604/408
(58) Field of Search ..................... 210/94, 95, 232, 210/238, 435, 445, 459, 460, 461, 486, 488, 446, 85; 285/93, 332; 604/406, 408, 410

(56) References Cited

U.S. PATENT DOCUMENTS

| | | |
|---|---|---|
| 2,765,923 | 10/1956 | Novak . |
| 3,191,600 | 6/1965 | Everett . |
| 3,506,130 * | 4/1970 | Shaye . |
| 3,799,702 | 3/1974 | Weishaar . |
| 4,035,304 * | 7/1977 | Watanabe . |
| 4,066,556 | 1/1978 | Vaillancourt . |
| 4,080,967 * | 3/1978 | O'Leary . |
| 4,173,222 | 11/1979 | Muetterties . |
| 4,191,204 | 3/1980 | Nehring . |
| 4,263,140 | 4/1981 | Wujnovich et al. . |
| 4,466,888 * | 8/1984 | Verkaart . |
| 4,798,590 | 1/1989 | O'Leary et al. . |
| 4,818,190 | 4/1989 | Pelmulder et al. . |
| 4,932,114 | 6/1990 | Morse et al. . |
| 4,954,251 * | 9/1990 | Barnes et al. . |
| 5,269,917 | 12/1993 | Stankowski . |
| 5,269,924 * | 12/1993 | Rochat . |
| 5,308,483 | 5/1994 | Sklar et al. . |
| 5,380,314 | 1/1995 | Herweck et al. . |
| 5,441,650 | 8/1995 | Kirsgalvis . |
| 5,573,526 * | 11/1996 | Hess . |
| 5,695,489 * | 12/1997 | Japuntich . |
| 5,827,429 * | 10/1998 | Ruschke et al. . |

FOREIGN PATENT DOCUMENTS

| | | |
|---|---|---|
| 0092313 | 10/1983 | (EP) . |
| 0623357 | 11/1994 | (EP) . |
| WO 95/17236 | 6/1995 | (WO) . |

* cited by examiner

*Primary Examiner*—John Kim
*Assistant Examiner*—David Sorkin
(74) *Attorney, Agent, or Firm*—Clark & Brody

(57) ABSTRACT

A system for collection of blood during surgery includes an interlock that requires conduits supplying collected blood to a bag to be properly connected before the system is operated. The interlock includes a source of electromagnetic energy that illuminates connectors to determine whether they are connected. In a preferred embodiment, the connector is a Luer connector with a cylindrical portion that redirects the electromagnetic energy when the connector is in place.

7 Claims, 3 Drawing Sheets

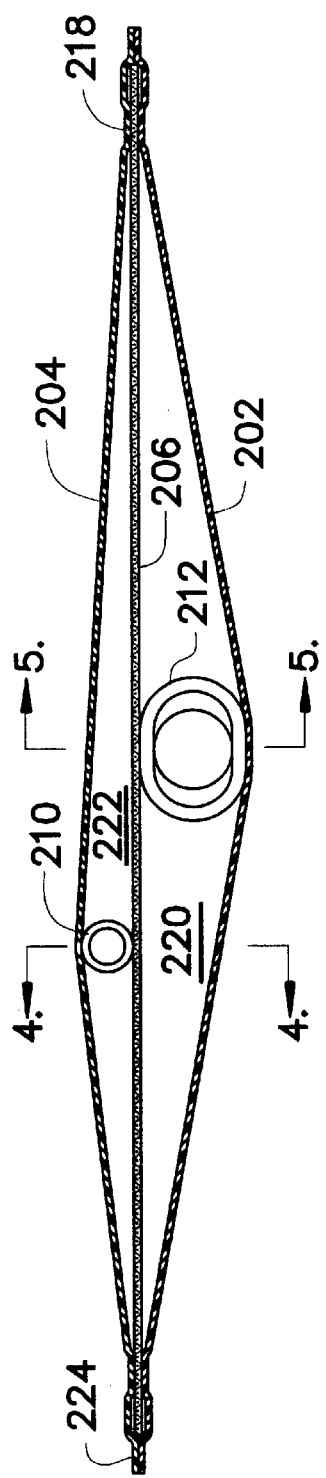
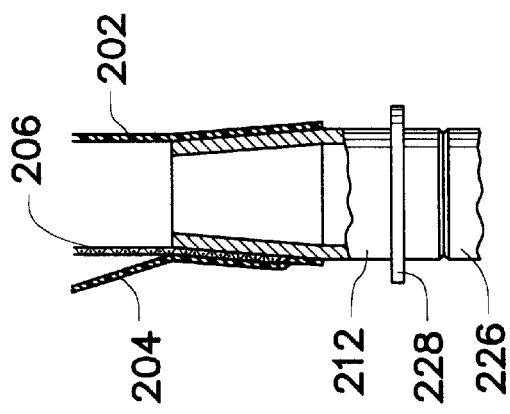
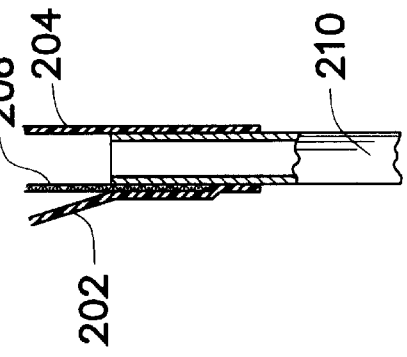
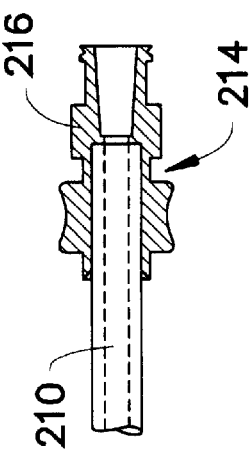

FILTER BAG AND CONNECTOR CARTRIDGE

CROSS REFERENCE TO RELATED APPLICATIONS

This application claims the benefit of provisional patent applications 60/008,127 filed Oct. 20, 1995; 60/008,128 filed Oct. 20, 1995; 60/005;772 filed Oct. 20, 1995; and 60/020,754 filed Jun. 28, 1996.

FIELD OF THE INVENTION

This invention relates to the art of systems for the collection of fluids. In particular, the invention relates to a bag for receiving fluids and a connector for connecting the bag to a supply pump.

BACKGROUND

It is known to collect fluids in containers such a flexible bags. For example, it is known to collect blood and other physiological fluids during surgery by pumping the blood into flexible bags. The fluids are then redelivered to the patient after processing. The fluids generally include debris that must be removed, and filters are used for this. Prior bags that include filters have not been effective, however, and are often expensive. Moreover, because the bags are disposable, the fluid lines are detachable, and it is necessary to provide an effective means for ensuring that the lines are properly connected before the pumping operation begins.

SUMMARY OF THE INVENTION

In accordance with the invention, a novel bag includes an internal filter, and a connector for attaching the bag to a fluid supply ensures that the bag is properly connected prior to operation of the pump.

The bag for receiving physiological fluids that have been recovered from a patient includes a filter for removing particles that are larger than a predetermined size. In the preferred embodiment, the filter is a 40$\mu$ mesh. The bag is made of two layers of flexible plastic with the filter held between the two layers. The inlet to the bag is placed between the filter and one of the outer layers, and the outlet is placed between the filter and the other of the outer layers. The flexible plastic layers and the filter are bonded together by heat, radio frequency (RF), or ultrasonic welding at the edges.

The edges are bonded in two locations. First, the filter and the outer layers are bonded completely around the bag inward of the outer edge of the bag, except for the locations where the inlet and outlet are secured. Then, the two outer layers and inlet and outlet conduits are bonded without the filter between them. By this construction, the bond of all three layers positions the filter to separate the bag into two compartments, and the outer bond acts as a safeguard to ensure that the contents are not spilled even if the inner bond fails.

In accordance with another aspect of the invention, a fluid supply line is connected to one or more lines, preferably inlet lines to the bag described above, by a verification connector. The verification connector includes means for verifying that the lines are properly connected and for controlling an interlock that prevents operation of the fluid pumps if the lines are not connected. The verification elements are easily attached to a base unit for cooperation with verification elements on the base unit to verify that the supply line is properly connected to the outlet lines. In the absence of such verification, operation of the fluid supply pump is inhibited. The verification connectors preferably include known Luer connectors for connecting the supply line to the inlet lines. Other types of connectors may, of course, be used.

In the preferred embodiment, the verification elements are optical. A light emitting diode, preferably infrared, and a photo detector, also preferably infrared, are contained in the base unit and are located with respect to the verification elements such that a beam from the light emitting diode will enter a transparent, conducting, portion of the verification elements when properly installed. The inlet line verification element will refract the light through an angle that will cause it to impinge on a detector in the base unit. Reflecting surfaces may be used to direct the incident and refracted beams to desired locations in the base unit. Signals from the photo detector are supplied to a control circuit that allows operation of a fluid supply pump only when the outlet lines are properly connected.

BRIEF DESCRIPTION OF THE DRAWINGS

FIG. 2 is a cross-section taken along line 2—2 of FIG. 1.

FIG. 3 is a cross-section taken along line 3—3 of FIG. 1.

FIG. 4 is a cross-section taken along line 4—4 of FIG. 2.

FIG. 5 is a cross-section taken along line 5—5 of FIG. 2.

DETAILED DESCRIPTION OF THE PREFERRED EMBODIMENT

Figure 1:
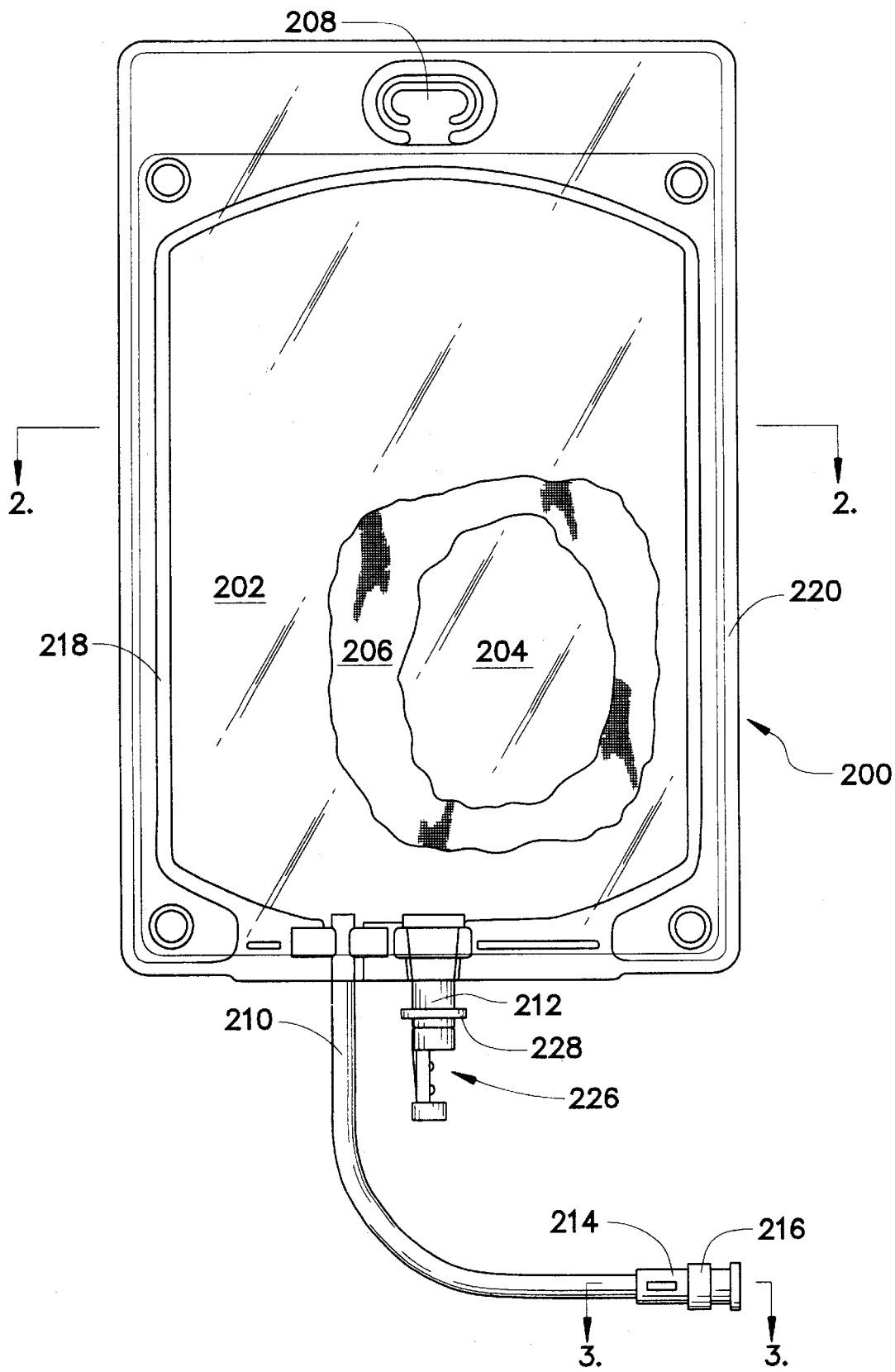
FIG. 1 is a front view of a filter bag, partially broken away, in accordance with the invention.

With reference to FIG. 1, a filter bag 200 is constructed of respective outer sheets 202 and 204. These sheets are preferably flexible and may be made of known plastic material. An inner sheet 206 is a filter, which is preferably a 40$\mu$ mesh of plastic material that can be easily bonded to the outer sheets. The bag includes an opening 208 to allow it to be hung from a variety of locations, such as a known I.V. stand.

The bag includes an inlet line 210 and an outlet port 212. The inlet line 210 includes a Luer connector 214 for attaching the line to a source of the physiological fluid, such as the supply line shown in FIG. 6. This connector is preferably designed to connect with other Luer connectors of standard size but also includes means for verifying whether the line is connected to a source of supply. While this verification element may take various forms, both electrical and mechanical, in the preferred embodiment the verification means is a cylindrical optical element 216. The cylinder is transparent to light, for example, infrared light from a light emitting diode. When the Luer connector is properly attached to the source of supply, the light passes through the cylinder and is refracted thereby to impinge on a detector. An electronic control circuit senses the presence of light on the detector and, in response, allows activation of a supply pump. This ensures that the line is connected to the source of supply, preventing inadvertently spilling the physiological fluids.

The preferred construction of the filter bag is more clearly shown in FIG. 2. The three layers of material, the two outer sheets 202, 204 and the filter 206, are bonded together at an inner bond 218. This bond, which may be produced by heating, radio frequency (RF), ultrasound, or other known methods, secures the three layers together to form two chambers 220 and 222 separated by the filter 206. A second, outer bond 224 is formed at the outer edge of the bag. This outer bond is between only the two outer sheets and excludes the filter material. The outer bond 224 provides an additional measure of safety to prevent separation of the two sheets and accidental discharge of the contents of the bag, should the inner bond fail. This is important in situations, such as pressure infusion, where the contents of the bag are subjected to pressures as high as 300 mmHg to increase the flow rate.

FIGS. 4 and 5 show how the sheets 202 and 204 and the filter 206 are secured to the inlet line 210 and the outlet 212. It will be appreciated that the inlet and outlet could as well be attached by a variety of means. For example, these could be provided by a known sidewall connector in each of the sheets 202 and 204.

In operation, physiological fluid, such as blood obtained from a surgical site, is supplied to the inlet line 210 by a pump (not sown). This fluid first flows through the inlet line 210 into the chamber 222. As the fluid passes through the filter into chamber 220, the filter removes unwanted particles. As the bag continues to fill, some of the fluid will remain in chamber 222, while the remainder will pass through the filter to chamber 220. When it is desired to use the fluid in the bag, an appropriate outlet line (not shown), such as an I.V. line is attached to the outlet 212 to permit fluid to flow out of the bag. Preferably, outlet 212 is a known spike port that has a removable cover 226 and receives a spike in known fashion.

The spike port includes a flange 228, which may be used to support the bag while it is being filled. When the fluid in the bag is withdrawn, the bag is hung from the opening 208, and the inlet line 210 is closed with a slide clamp, metal crimp, Luer cap, or the like. Thus, the bag is filled in an orientation opposite from the orientation from which it is emptied. This increases efficiency by providing even usage of the filter layer; the in-flowing fluid will pass continuously through one end of the filter as it is filling and the out-flowing fluid will continuously pass through the opposite end of the filter as it is being discharged.

Figure 6:
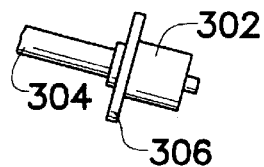
FIG. 6 is a perspective of a male Luer connector with a mounting key attached.
Figure 7:
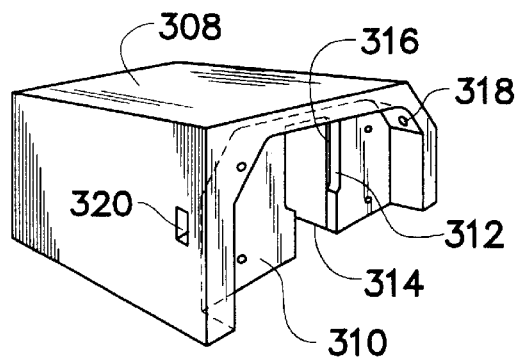
FIG. 7 is a perspective of a base element having verification components in accordance with the invention.

With reference to FIG. 6, a male Luer connector 302 is attached to a tube 304, as known in the art. A mounting key 306 according to the invention is attached to the Luer connector, as by welding or cement. The key is used to secure the male connector to the base element shown in FIGS. 7 through 10. The base element 308 is attached to, or is a part of, apparatus for pumping fluids into a bag, such as bag 200. The base element includes a face plate 310 for receiving the key 306 and the Luer connector. The face plate includes an opening 312, which is of a shape that will allow the key to be inserted. A narrower notch 314 is located below the opening 312, and a slot 316 is formed between the front of the faceplate and a rear wall thereof. Slot 316 extends vertically from the bottom of the opening 312 to just above the bottom of the faceplate. While the key has been shown to be square, other shapes are possible.

Figure 8A:
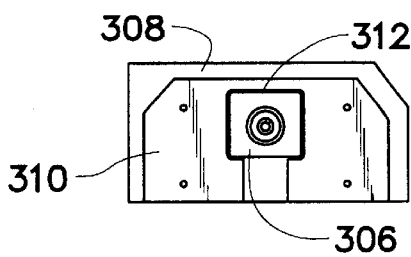
FIGS. 8A and 8B are front views of the base element illustrating attachment of the mounting key to the base element.
Figure 8B:
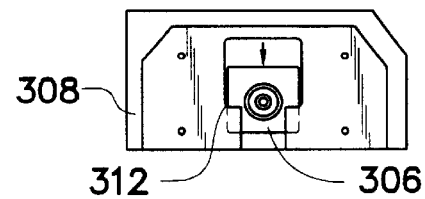

The installation of the key will be explained with reference to FIGS. 8A and 8B. The key 306 with the male Luer connected is first inserted in the opening 312 as shown in FIG. 8A. Then, the key is slid downward as illustrated in FIG. 8B, whereby the edges of the key engage the slot 316 to thereby secure the male Luer and key in the faceplate 310. The key is preferably retained in the position shown in FIG. 8B by gravity; as well the position may be maintained by friction or other mechanisms.

The purpose of this structure is to provide verification of the proper installation of the Luer connectors. Thus, base element 308 includes a source 318 of electromagnetic energy, such as infrared energy from a light emitting diode. The base also includes a window 320 for allowing refracted energy to impinge on a detector 322. The detector is shown located behind the window, but it could be placed in the element 308 as well. Also, reflectors could be employed to direct the beams as desired to detectors located elsewhere.

Figure 9A:
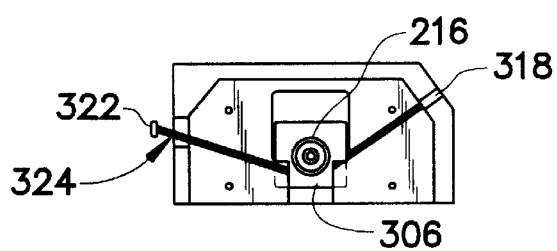
FIGS. 9a and 9B illustrate the operation of the verification elements.

FIG. 9A illustrates the situation when the female Luer connector 214 is attached to the male Luer connector 302, and the key 306 is secured in the faceplate 310. In this configuration, the light beam 324 is refracted by the optical element 216 on the female Luer. Thus, the light path is as shown in FIG. 9A where is passes through window 320 and impinges on detector 322. The detector 322 supplies a signal to a control circuit allowing the pumps to operate.

Figure 9B:
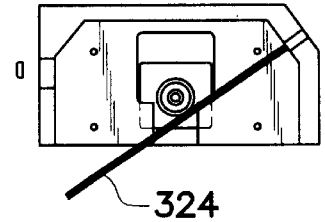

FIG. 9B illustrates the situation where the female Luer is not properly connected. In this situation, the required refraction does not occur, and the beam does not pass through the window 324. Accordingly, the detector 322 does not detect the impingement, and the control circuit does not enable operation of the pumps.

Figure 10:
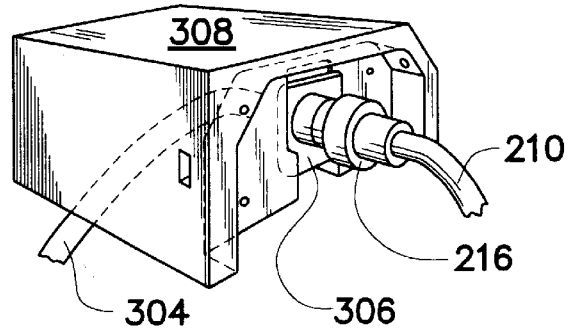
FIG. 10 is a perspective showing the fluids lines properly connected and attached to the base element.

FIG. 10 shows the male and female Luer connectors attached to each other and installed on the base element. The base element provides an opening at the bottom for receiving the line 304 from the source of fluid, such as a pump. The line 304 and key may be installed from the front of the base element prior to connection of the line 210. Or, the two lines may be attached and then installed in the base element. One advantage of the key, however, is that the connector 214 may be easily attached to the connector 302 with one hand when the key is secure in the base element.

While any number of inlet lines 210 may be used, only one is illustrated in the figures. Thus, supply line 304 may be connected to a Y-connector (not shown), which is in turn connected to the supply pump As described above, each of the inlet lines 210 includes a female Luer connector 214 that has been modified to include a verification element. The verification element in the preferred embodiment is the optical element 216 that cooperates with the light source and detector in the base element to verify that the connector 214 is properly in place.

It will be appreciated that the described verification system is fail-safe because it requires a predetermined signal to be received by the photo detectors before connection is verified. If the Luer connectors are not in place, the light from the source in the base unit will not be refracted to the photo detectors, and verification will be precluded. Modifications within the scope of the claims will be apparent to those of skill in the art.

We claim:

1. Apparatus for connecting two fluid lines comprising:
   a first connector and a first of said fluid lines attached thereto,
   a second connector and a second of said fluid lines connected thereto, said second connector being adapted to connect with said first connector to connect said two fluid lines, a source of electromagnetic energy arranged to direct said electromagnetic energy toward the location of said second connector when said second connector is connected to said first connector, and a detector arranged to detect said electromagnetic energy only when said second connector is connected to said first connector.

2. Apparatus according to claim 1 wherein said source of electromagnetic energy forms at least one optical channel for directing a beam of light toward said second connector means when said second connector means is attached to said first connector means.

3. Apparatus according to claim 2 wherein said at least one optical channel comprises an inlet channel positioned to align with said source of electromagnetic energy and an outlet channel positioned to align with said detector.

4. Apparatus according to claim 1 wherein said second connector comprises an optical element positioned to be irradiated by said electromagnetic energy when said second connector is connected to said first connector.

5. Apparatus according to claim 4 wherein said optical element is a transparent cylinder.

6. Apparatus according to claim 5 wherein said second connector comprises a Luer connector.

7. Apparatus according to claim 6 wherein said transparent cylinder is coaxial with said Luer connector.

* * * * *